US012109095B2

(12) United States Patent
Tomita et al.

(10) Patent No.: US 12,109,095 B2
(45) Date of Patent: Oct. 8, 2024

(54) ABSORBENT ARTICLE

(71) Applicant: Kao Corporation, Tokyo (JP)

(72) Inventors: Mina Tomita, Utsunomiya (JP); Takeshi Suzuki, Sano (JP); Ayako Makino, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 1204 days.

(21) Appl. No.: 16/758,783

(22) PCT Filed: Oct. 11, 2018

(86) PCT No.: PCT/JP2018/037974
§ 371 (c)(1),
(2) Date: Apr. 23, 2020

(87) PCT Pub. No.: WO2019/082677
PCT Pub. Date: May 2, 2019

(65) Prior Publication Data
US 2021/0177668 A1  Jun. 17, 2021

(30) Foreign Application Priority Data

Oct. 25, 2017 (JP) ................................. 2017-206579
Aug. 10, 2018 (JP) ................................. 2018-152014

(51) Int. Cl.
*A61F 13/511* (2006.01)
*A61F 13/475* (2006.01)
*A61F 13/514* (2006.01)

(52) U.S. Cl.
CPC ...... *A61F 13/51104* (2013.01); *A61F 13/475* (2013.01); *A61F 13/5116* (2013.01); *A61F 13/514* (2013.01)

(58) Field of Classification Search
CPC .......................... A61F 13/51104; A61F 13/511
See application file for complete search history.

(56) References Cited

U.S. PATENT DOCUMENTS 6,156,022 A * 12/2000 Hedlund ............... A61F 13/495
604/385.29
2005/0148970 A1 7/2005 Kudo et al.
(Continued)

FOREIGN PATENT DOCUMENTS

CN 203447435 A 2/2014
CN 205411476 U 8/2016
(Continued)

OTHER PUBLICATIONS

International Search Report for PCT/JP2018/037974 (PCT/ISA/210) mailed on Dec. 25, 2018.
(Continued)

*Primary Examiner* — Jessica Arble
(74) *Attorney, Agent, or Firm* — Birch, Stewart, Kolasch & Birch, LLP

(57) ABSTRACT

An absorbent article includes: a topsheet including a projecting-and-depressed region; a backsheet; and an absorbent member arranged between the topsheet and the backsheet. The absorbent article has a longitudinal direction that corresponds to a front-rear direction of a wearer and a width direction that is orthogonal to the longitudinal direction. A plurality of slanting projections (41) are formed in the projecting-and-depressed region (P). The slanting projections (41) project toward the wearer's skin side, and the position of the apex (t) of each slanting projection is deviated toward one side in the longitudinal direction (X) from the central position (41c) located between both ends of the slanting projection (41) in the longitudinal direction (X).

18 Claims, 9 Drawing Sheets

(56) References Cited

U.S. PATENT DOCUMENTS

| | | |
|---|---|---|
| 2010/0249740 A1 | 9/2010 | Miyamoto et al. |
| 2013/0158497 A1 | 6/2013 | Yamaguchi et al. |
| 2016/0074240 A1 | 3/2016 | Rosati et al. |
| 2016/0220421 A1 | 8/2016 | Kuramochi |
| 2017/0105888 A1 | 4/2017 | Kimura et al. |
| 2017/0312144 A1 | 11/2017 | Moritani |

FOREIGN PATENT DOCUMENTS

| | | | | |
|---|---|---|---|---|
| CN | 205586162 U | | 9/2016 | |
| CN | 106163472 A | | 11/2016 | |
| CN | 107072831 A | | 8/2017 | |
| CN | 107106363 A | | 8/2017 | |
| CN | 107106364 A | | 8/2017 | |
| EP | 2 656 826 A1 | | 10/2013 | |
| GB | 2559705 A | | 8/2018 | |
| JP | 2004121701 A | * | 4/2004 | |
| JP | 2009-160035 A | | 7/2009 | |
| JP | 2011-15707 A | | 1/2011 | |
| JP | 2016-8367 A | | 1/2016 | |
| JP | 2016-96926 A | | 5/2016 | |
| JP | 2016116847 A | * | 6/2016 | ............ A61F 13/49 |
| JP | 2016-168299 A | | 9/2016 | |
| JP | 2016-209535 A | | 12/2016 | |
| JP | 2017-86706 A | | 5/2017 | |
| JP | 2017-93732 A | | 6/2017 | |
| JP | 2017-99593 A | | 6/2017 | |
| JP | 2017-153915 A | | 9/2017 | |
| RU | 2405517 C2 | | 8/2010 | |
| TW | 201540274 A | | 11/2015 | |
| WO | WO 2012/014957 A1 | | 2/2012 | |
| WO | WO 2012/086487 A1 | | 6/2012 | |
| WO | WO 2015/045842 A1 | | 4/2015 | |
| WO | WO 2016/098848 A1 | | 6/2016 | |
| WO | WO 2017/086076 A1 | | 5/2017 | |

OTHER PUBLICATIONS

International Search Report for International Application No. PCT/JP2018/042535, dated Jan. 22, 2019, with an English translation.

* cited by examiner

ABSORBENT ARTICLE

TECHNICAL FIELD

The present invention relates to absorbent articles, such as disposable diapers, urine collection pads, incontinence pads, and sanitary napkins.

BACKGROUND ART

A conventionally known technique involves forming the skin-facing surface side of a topsheet of an absorbent article, such as a disposable diaper, into a three-dimensional shape, with the aim of, for example, inhibiting excrement from flowing on the topsheet or controlling the flowing direction in a specific direction.

For example, Patent Literature 1 discloses a nonwoven fabric used as, for example, a topsheet of a disposable diaper, the nonwoven fabric including a base portion that spreads out substantially in a planar manner, and a plurality of projections projecting from the base portion. Each projection includes: a peripheral surface portion that stands up from the base portion and forms a peripheral surface; and a top portion formed on the tip end side of the peripheral surface portion. The peripheral surface portion has, in at least a portion of its peripheral surface, a protruding portion that protrudes outward.

Further, Applicant has also previously proposed using, as a topsheet of an absorbent article, a composite sheet including layered first and second sheets that are joined together at a plurality of joined portions, wherein the first sheet forms projections that project in a direction separating from the second sheet at sections other than the joined portions, thus projecting toward the wearer's skin side (Patent Literature 2 etc.).

CITATION LIST

Patent Literature

Patent Literature 1: JP 2016-8367A
Patent Literature 2: JP 2017-93732A

SUMMARY OF INVENTION

The present invention is an absorbent article including: a topsheet including a projecting-and-depressed region; a backsheet; and an absorbent member arranged between the topsheet and the backsheet. The absorbent article has a longitudinal direction that corresponds to a front-rear direction of a wearer and a width direction that is orthogonal to the longitudinal direction. A plurality of slanting projections are formed in the projecting-and-depressed region. The slanting projections project toward the wearer's skin side, and a position of an apex of each slanting projection is deviated toward one side in the longitudinal direction from a central position located between both ends of the slanting projection in the longitudinal direction.

DESCRIPTION OF EMBODIMENTS

Patent Literature 1 describes as follows. In the nonwoven fabric proposed in Patent Literature 1, the peripheral surface portion of each projection has a protruding portion that protrudes outward from the peripheral surface. Thus, the protruding portion can block the flow of liquid in cases where, for example, the nonwoven fabric is tilted; as a result, liquid is suppressed from flowing on the nonwoven fabric, and the liquid can permeate and be absorbed efficiently.

In the nonwoven fabric of Patent Literature 1, the projections are made stiff so they can maintain their projecting shape even when pressurized. This, however, has a drawback that, for example, in cases where the excrement is soft feces which has a relatively high viscosity, the excrement remaining between the projections tends to adhere to the wearer's skin.

On the other hand, a topsheet made of the composite sheet disclosed in Patent Literature 2 has good air permeability and liquid capturability, but is still insufficient in terms of controlling the flow of excrement such as soft feces and preventing the excrement remaining on the topsheet from adhering to the wearer's skin.

The present invention thus relates to an absorbent article capable of overcoming drawbacks of the aforementioned conventional art.

The present invention is described below according to preferred embodiments thereof with reference to the drawings.

Figure 1:
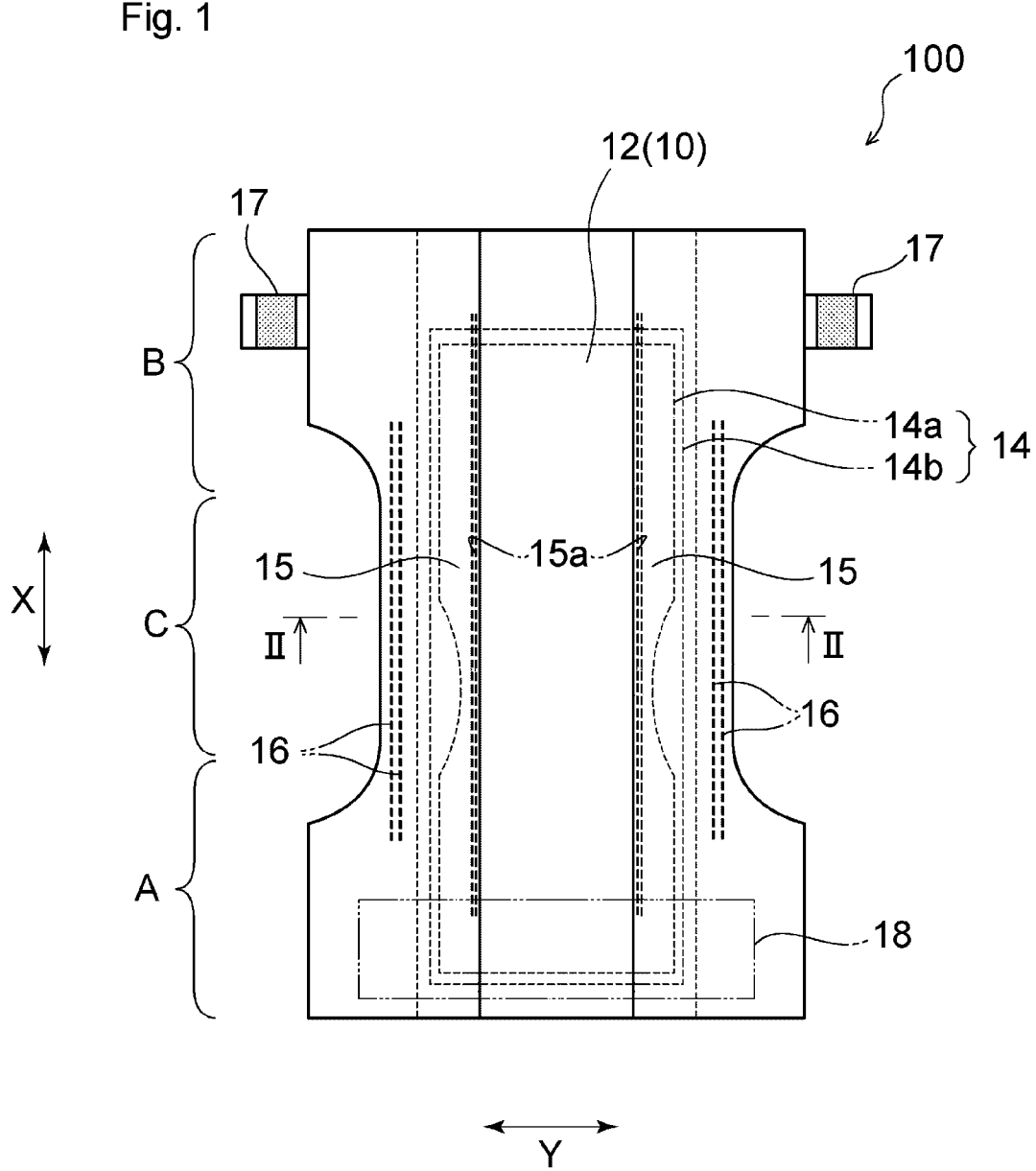
FIG. 1 is a plan view illustrating a basic configuration of a disposable diaper as an embodiment of an absorbent article of the present invention.
Figure 2:
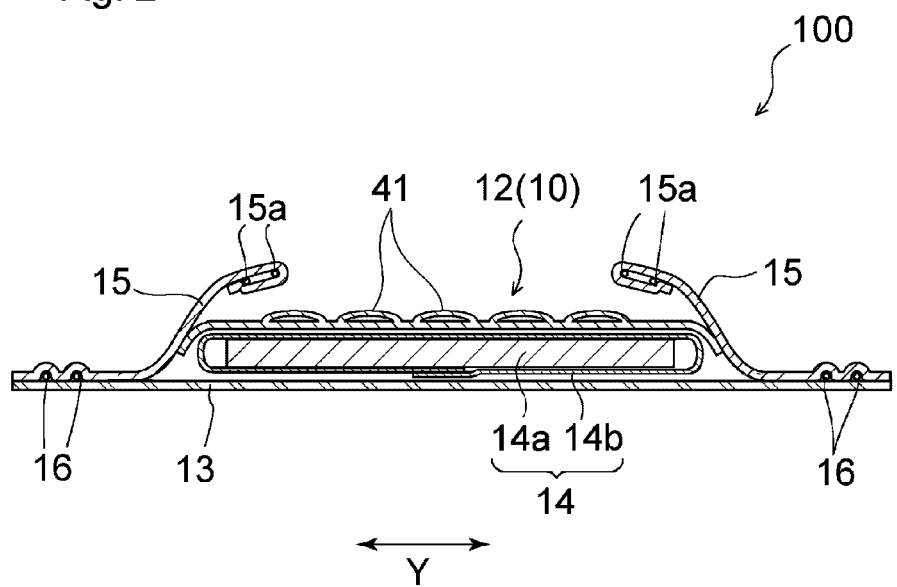
FIG. 2 is a cross-sectional view taken along line II-II of FIG. 1.

FIGS. 1 and 2 illustrate a basic structure of a disposable diaper 100 (also referred to simply as "diaper 100") which is an embodiment of an absorbent article of the present invention.

As illustrated in FIGS. 1 and 2, the diaper 100 includes: a liquid-permeable topsheet 12; a liquid-impermeable backsheet 13; and an absorbent member 14 arranged between the two sheets 12, 13. In relation to the backsheet 13, "liquid-impermeable" is a concept encompassing "sparingly liquid-permeable"; the concept also encompasses cases where the backsheet 13 does not allow passage of liquid at all, and cases where the backsheet is made of a water-repellent sheet etc.

The diaper 100 has: a longitudinal direction X corresponding to the front-rear direction of a wearer; and a width direction Y orthogonal to the longitudinal direction X in a state where the diaper 100 is spread out in a plane as illustrated in FIG. 1. When the diaper's entire length in the longitudinal direction X is divided into three equal parts, the diaper 100 can be divided into: a front portion A to be arranged on the wearer's front side when the diaper is worn; a rear portion B to be arranged on the wearer's rear side when the diaper is worn; and a crotch portion C located between the front portion A and the rear portion B. The diaper 100 is an open-type disposable diaper; fastening tapes 17 are provided to the respective lateral side edge portions of the rear portion B, and a landing zone 18 for fastening the fastening tapes 17 is provided on the outer surface of the front portion A.

The absorbent member 14 in the diaper 100 includes an absorbent core 14a, and a core-wrap sheet 14b enveloping the absorbent core 14a. The absorbent core 14a may be made of, for example, a fiber stack including a liquid-absorbing fiber such as pulp fiber, or a mixed fiber stack including a liquid-absorbing fiber and a water-absorbent polymer. Examples of the liquid-absorbing fiber include cellulose-based hydrophilic fibers, such as pulp fiber, rayon fiber, cotton fiber, and cellulose acetate. Other than cellulose-based hydrophilic fibers, it is also possible to use fiber made of a synthetic resin, such as a polyolefin, a polyester, or a polyamide, and hydrophilized by a surfactant, for example. For the core-wrap sheet 14b, it is possible to use, for example, tissue paper or a water-permeable nonwoven fabric. A single core-wrap sheet 14b may envelop the entire absorbent core 14a, or two or more sheets may be used in combination to envelop the absorbent core 14a. For the backsheet 13, it is possible to use, for example, a liquid-impermeable or water-repellent resin film, or a laminate sheet of a resin film and a nonwoven fabric.

Leak-proof-cuff-forming sheets 15, each including elastic members 15a, are provided to each of both sides, along the longitudinal direction X, of the diaper 100, and, by contraction of the elastic members 15a, leak-proof cuffs that stand up toward the wearer's skin side are formed in the crotch portion C in a state where the diaper is worn. In sections surrounding the legs in the crotch portion C, leg-portion elastic members 16 are provided in a stretched state, and by contraction of the leg-portion elastic members, leg gathers that improve fittability around the wearer's legs are formed in the crotch portion C in a state where the diaper is worn.

Figure 3:
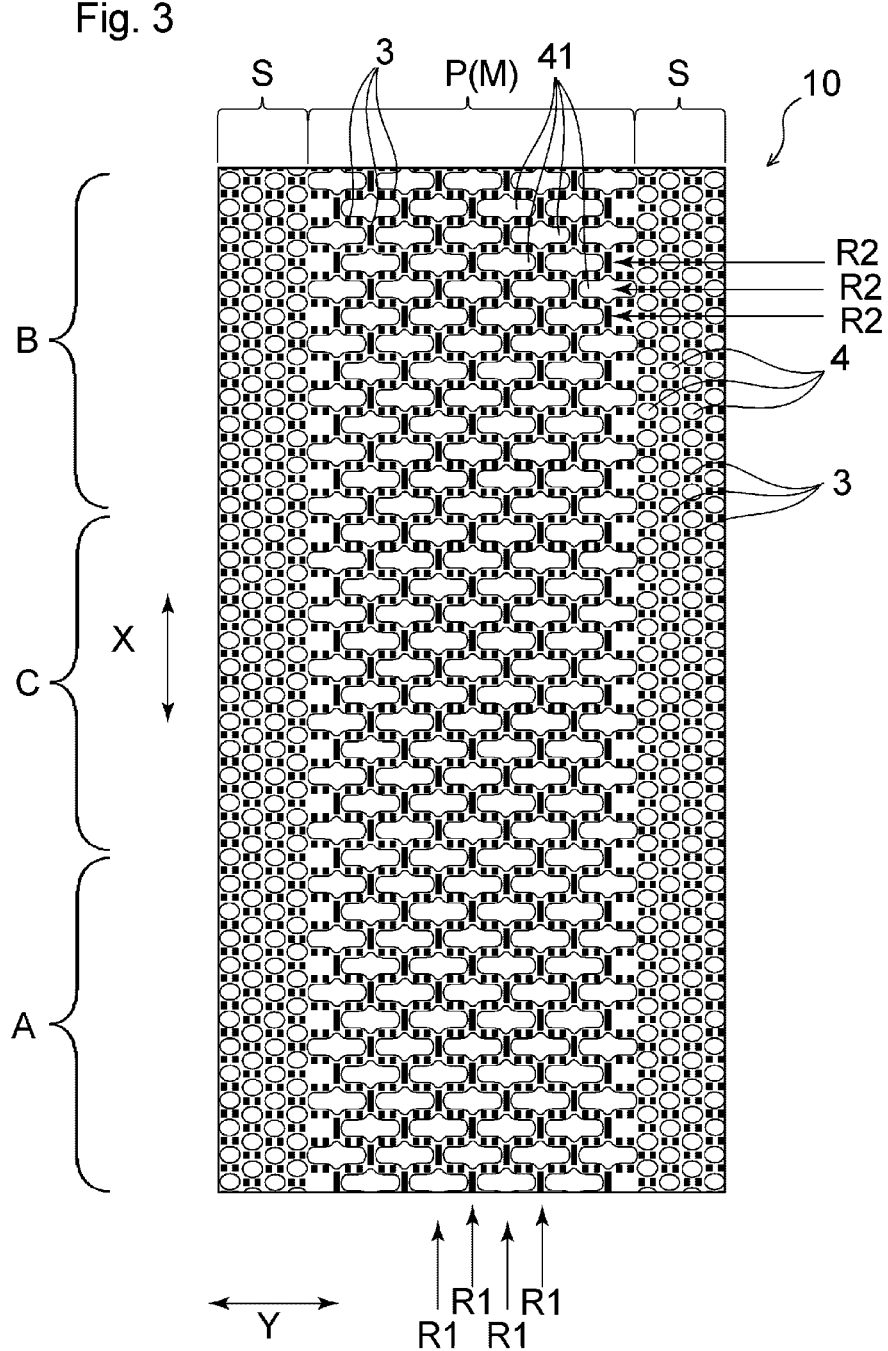
FIG. 3 is a plan view illustrating a topsheet (composite sheet) of the disposable diaper of the first embodiment.

The topsheet 12 of the disposable diaper 100 of the first embodiment is constituted by a composite sheet 10, as illustrated in FIG. 3.

As illustrated in FIG. 3, the composite sheet 10 includes: a central region M located in a central area in the width direction Y; and a pair of side regions S, S located on both sides of the central region M. The central region M forms the projecting-and-depressed region P in the topsheet 12.

The projecting-and-depressed region P is a region wherein a plurality of slanting projections 41 constituted by a fiber sheet, such as a nonwoven fabric, are formed. It is preferable that, as illustrated in FIG. 3, the slanting projections are formed in a dispersed state in the longitudinal direction X and the width direction Y according to a predetermined pattern.

Figure 5A:
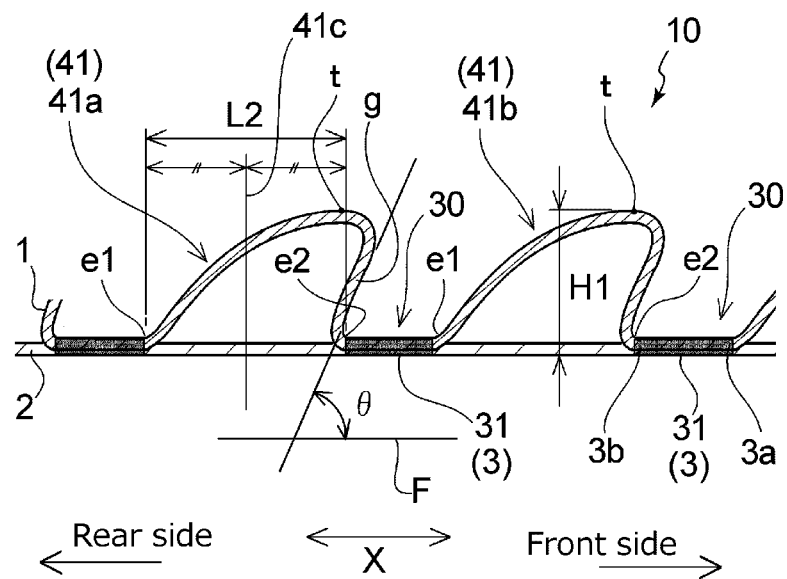
FIG. 5 shows enlarged cross-sectional views each illustrating a cross section along the thickness direction of the topsheet (composite sheet) illustrated in FIG. 3, wherein FIG. 5(*a*) is a cross-sectional view taken along line of FIG. 4 and passing through the apex of a slanting projection, and FIG. 5(*b*) is a cross-sectional view taken along line IV-IV of FIG. 4.

As illustrated in FIG. 5(a), the slanting projection 41 is a projection that projects toward the wearer's skin side, and the position of the apex t of each projection is deviated toward one side in the longitudinal direction X from the central position 41c located between both ends e1, e2 of the slanting projection 41 in the longitudinal direction X. The aforementioned both ends e1, e2 of the slanting projection 41 are the ends thereof in a cross section along the longitudinal direction X of the absorbent article, and preferably in a cross section passing through the apex t. These ends are rising base ends from which the slanting projection 41 rises up.

The "one side" toward which the position of the apex t is deviated is either the front side (lower side in FIG. 1) or the rear side (upper side in FIG. 1) in the longitudinal direction X of the absorbent article, and, as illustrated in FIG. 5(a), the projection may be a slanting projection whose position of the apex t is deviated toward the front side from the central position 41c, or may be a slanting projection whose position of the apex t is deviated toward the rear side from the central position 41c (not illustrated). Hereinbelow, a slanting projection 41 whose position of the apex t is deviated toward the front side from the central position 41c is also referred to as a "forward slanting projection", and a slanting projection whose position of the apex t is deviated toward the rear side from the central position 41c is also referred to as a "rearward slanting projection".

When the length L2 (see FIG. 5(a)) between the aforementioned both ends e1, e2 of the slanting projection 41 is defined as 100%, the position of the apex t of the slanting projection 41 is preferably located outside a range covering a distance of 5% in front and rear of the central position 41c, and is more preferably located outside a range covering a distance of 10% in front and rear of the central position 41c.

In the composite sheet 10 of the disposable diaper 100 of the first embodiment, slanting projections, which are forward slanting projections, are formed over the entire region of the central region M in which the projecting-and-depressed region P is formed, and, in the projecting-and-depressed region P of the topsheet 12, the forward slanting projections are formed in the section located in the rear portion B, the section located in the crotch portion C, and the section located in the front portion A. Instead, forward slanting projections, whose position of the apex t is deviated toward the front side, may be formed in the section located in the rear portion B of the topsheet 12, and rearward slanting projections, whose position of the apex t is deviated toward the rear side, may be formed in the section located in the front portion A. Further, either forward slanting projections or rearward slanting projections may be formed in the crotch portion C, or non-slanting projections, whose position of the apex t is present at the central position located between the projection's both ends, may be formed.

Alternatively, assuming that the disposable diaper 100 is divided into two regions along a widthwise central line that divides the diaper's entire length in the longitudinal direction in two equal parts, forward slanting projections may be formed in one region on the rear side whereas rearward slanting projections may be formed in the other region on the front side.

Figure 6A:
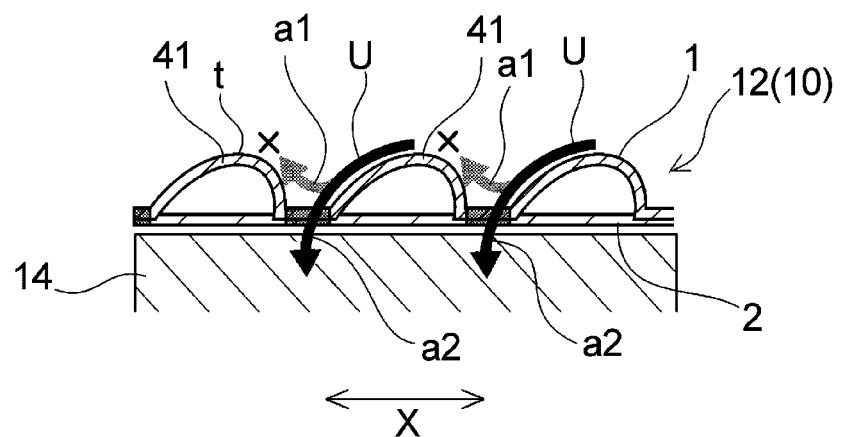
FIG. 6 shows diagrams illustrating effects of the present invention, wherein FIG. 6(*a*) is a diagram illustrating actions/operations of the present invention, and FIG. 6(*b*) is a diagram illustrating actions/operations of conventional art.

The disposable diaper 100 of the first embodiment includes the aforementioned projecting-and-depressed region P having a plurality of slanting projections 41 formed therein. Thus, as illustrated in FIG. 6(a), the migration, on the topsheet 12, of excrement U supplied onto the topsheet 12 is effectively inhibited in the projecting-and-depressed region P because the slanting projections 41 function as leak-proof barriers as illustrated by arrows a1, thereby being able to effectively suppress diffusion of excrement U on the topsheet 12. Thus, it is possible to effectively suppress the excrement U from moving on the topsheet 12 and getting diffused toward undesired sections/directions.

For example, as in the present embodiment, by providing forward slanting projections in the section located in the rear portion B of the topsheet 12, excrement such as soft feces can be effectively suppressed from leaking out from the rear side. Further, by providing rearward slanting projections in the section located in the front portion A of the topsheet 12, excrement such as soft feces can be effectively suppressed from leaking out from the front side. Note that, in the topsheet 12 of the present invention may include, over the entire topsheet 12 or over the entire central region M, only either the forward slanting projections or the rearward slanting projections.

In the present embodiment, the periphery of each of the slanting projections 41 is surrounded by a depression 30 (see FIG. 5) in which joined portions 3 are formed intermittently in the bottom portion thereof. As illustrated by arrows a2, the excrement U can easily migrate into the absorbent member 14 through sections other than the joined portions 3 in the bottom portion of the depressions 30. This configuration further improves the effect of suppressing diffusion of excrement U toward undesired sections/directions.

Figure 6B:
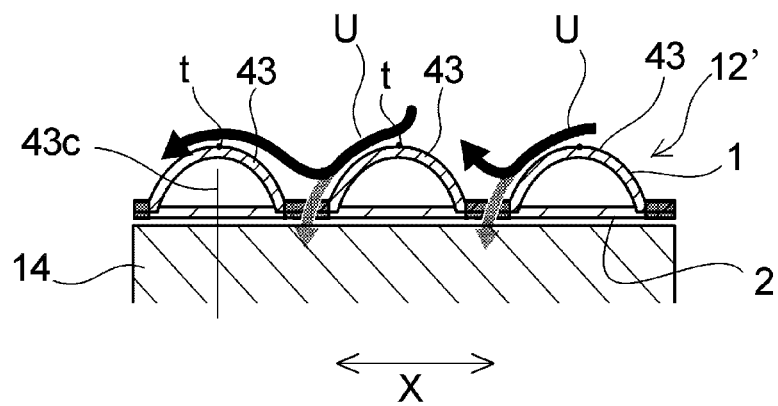

In contrast, in cases of non-slanting projections 43 whose position of the apex t is present at the central position 43c located between both ends thereof in the longitudinal direction X, excrement U, such as urine or soft feces, supplied onto the topsheet 12' is likely to move over the non-slanting projections 43 as illustrated in FIG. 6(b), thereby making it difficult to sufficiently control diffusion of excrement U.

Figure 7A:
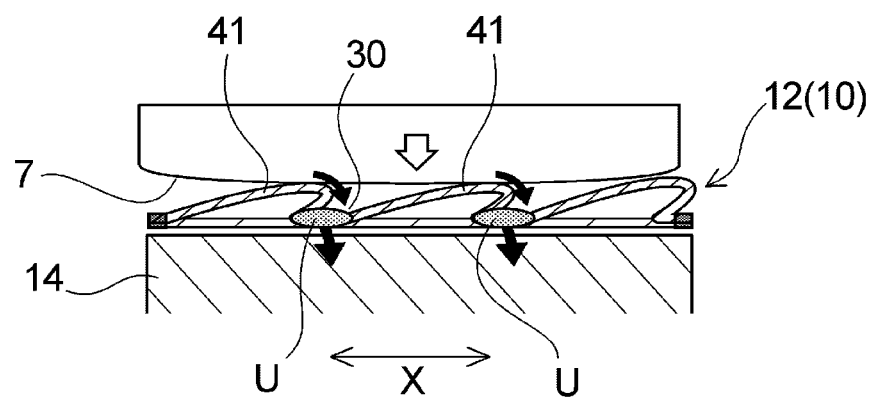
FIG. 7 shows diagrams illustrating effects of the present invention, wherein FIG. 7(*a*) is a diagram illustrating actions/operations of the present invention, and FIG. 7(*b*) is a diagram illustrating actions/operations of conventional art.

Further, in cases where the topsheet 12 includes a projecting-and-depressed region P including a plurality of slanting projections 41 as in the present embodiment, as illustrated in FIG. 7(a), when the slanting projections 41 are pressurized by the wearer's skin 7 in a state where excrement U is accumulated in the depressions 30 between the slanting projections 41, the slanting projections 41 are likely to tilt in a state so as to cover a wide area over the excrement U. Further, in the thus-tilted slanting projections 41, sections where no excrement U is attached are likely to contact the wearer's skin 7. Thus, adhesion of excrement U to the wearer's skin 7 is also prevented.

Furthermore, when the slanting projections 41 are tilted in a state so as to cover a portion or the entirety of the excrement U, a portion of the excrement U is pressed-in toward the absorbent member 14 side by the slanting projections 41.

As described above, in the projecting-and-depressed region P in which the slanting projections 41 are formed, excrement remaining in the depressions 30 between the projections can efficiently be made less prone to adhere to the wearer's skin.

This effect is achieved more reliably in cases where: the periphery of each slanting projection 41 is surrounded by the aforementioned depression 30 (see FIG. 5) in which the joined portions 3 are formed intermittently in the bottom portion; and excrement U is allowed to migrate easily toward the absorbent member 14 through sections other than the joined portions 3 in the bottom portion of the depression 30.

Figure 7B:
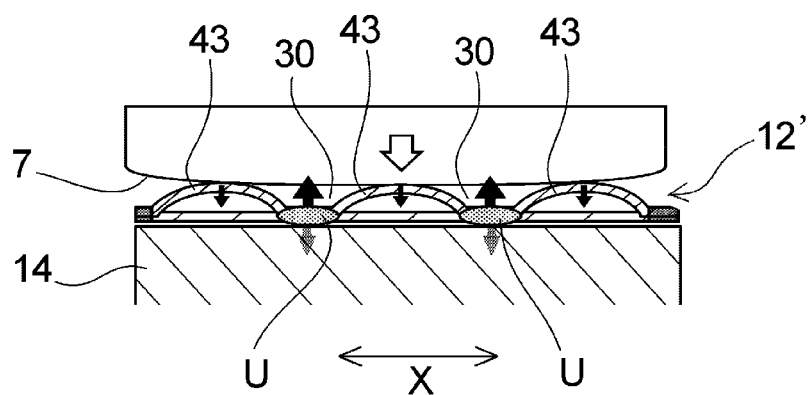

In contrast, in cases of conventional non-slanting projections 43 whose position of the apex t is present at the central position 43c located between both ends thereof in the longitudinal direction X, as illustrated in FIG. 7(b), when the topsheet 12' is pressurized by the wearer's skin 7 in a state where excrement U is accumulated in the depressions 30 between the non-slanting projections 43, the excrement U easily adheres to the wearer's skin 7. Note that, in cases where the non-slanting projections 43 are made stiff in order to suppress the excrement U accumulated in the depressions 30 between the non-slanting projections 43 from adhering to the wearer's skin 7, the projections 43 are not able to achieve the effect of pressing-in the excrement U.

Figure 5B:
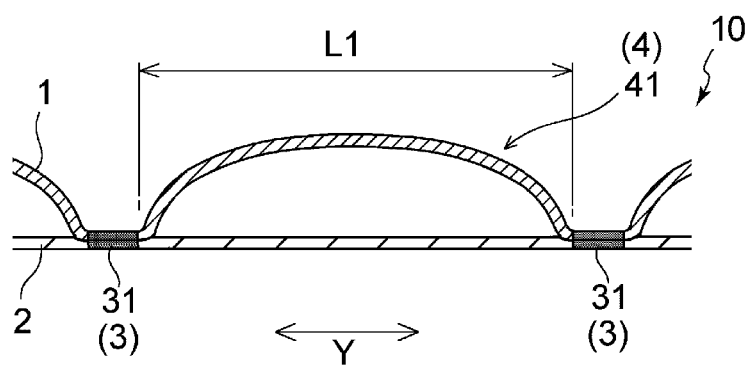

From the viewpoint of achieving one or more of the aforementioned effects more reliably, it is preferable that the slanting projection 41 present in the projecting-and-depressed region P is slanted in a state in which a rising section g of the slanting projection 41 on the one side in the longitudinal direction X, toward which the position of the apex t is deviated, is tilted more toward the one side than perpendicular, like the slanting projection 41a illustrated in FIG. 5. Herein, "perpendicular" means "perpendicular to a plane (plane orthogonal to the thickness direction) F extending parallel to a surface of the topsheet 12". A "state tilted more toward the one side than perpendicular" refers to: a state tilted toward the front side in cases where the position of the apex t of the slanting projection is deviated toward the front side from the central position 41c like the slanting projection 41a illustrated in FIG. 5; and a state tilted toward the rear side in cases where the position of the apex t of the slanting projection 41 is deviated toward the rear side from the central position 41c.

The slanting projection 41a illustrated in FIG. 5 is slanted in a state where the rising section g on the front side in the longitudinal direction X, toward which the position of the apex t is deviated, is tilted more toward the front side than perpendicular, and the slanting projection 41a includes an overhanging section on the front side (one side) toward which the position of the apex t is deviated. Thus, when the topsheet 12 is pressurized by the wearer's skin 7, the slanting projections 41 can easily tilt in a state so as to cover a wide area over the excrement U, and thus, adhesion of excrement U to the wearer's skin is prevented more effectively.

When the slanting angle perpendicular to a plane (plane orthogonal to the thickness direction) F extending parallel to a surface of the topsheet 12 is defined as 90°, the slanting angle θ of the rising section g of the slanting projection 41 is preferably less than 90°, more preferably 30° or greater and less than 80°, even more preferably from 45° to 60°.

From the viewpoint of preventing the slanting projections 41 from covering up the depressions 30 in advance, it is preferable that, like the slanting projection 41a illustrated in FIG. 5(a), the position of the apex t of the slanting projection 41 does not go beyond the position of another slanting projection 41b's end e1 that is located on the opposite side (rear side) from the one side (front side), the other slanting projection 41b being adjacent to the slanting projection 41a on the one side (front side) toward which the position of the apex t is deviated. In this way, excrement U can easily enter the depressions 30 between the slanting projections 41, thereby improving, for example, migratability of the excrement U into the absorbent member 14.

Figure 4:
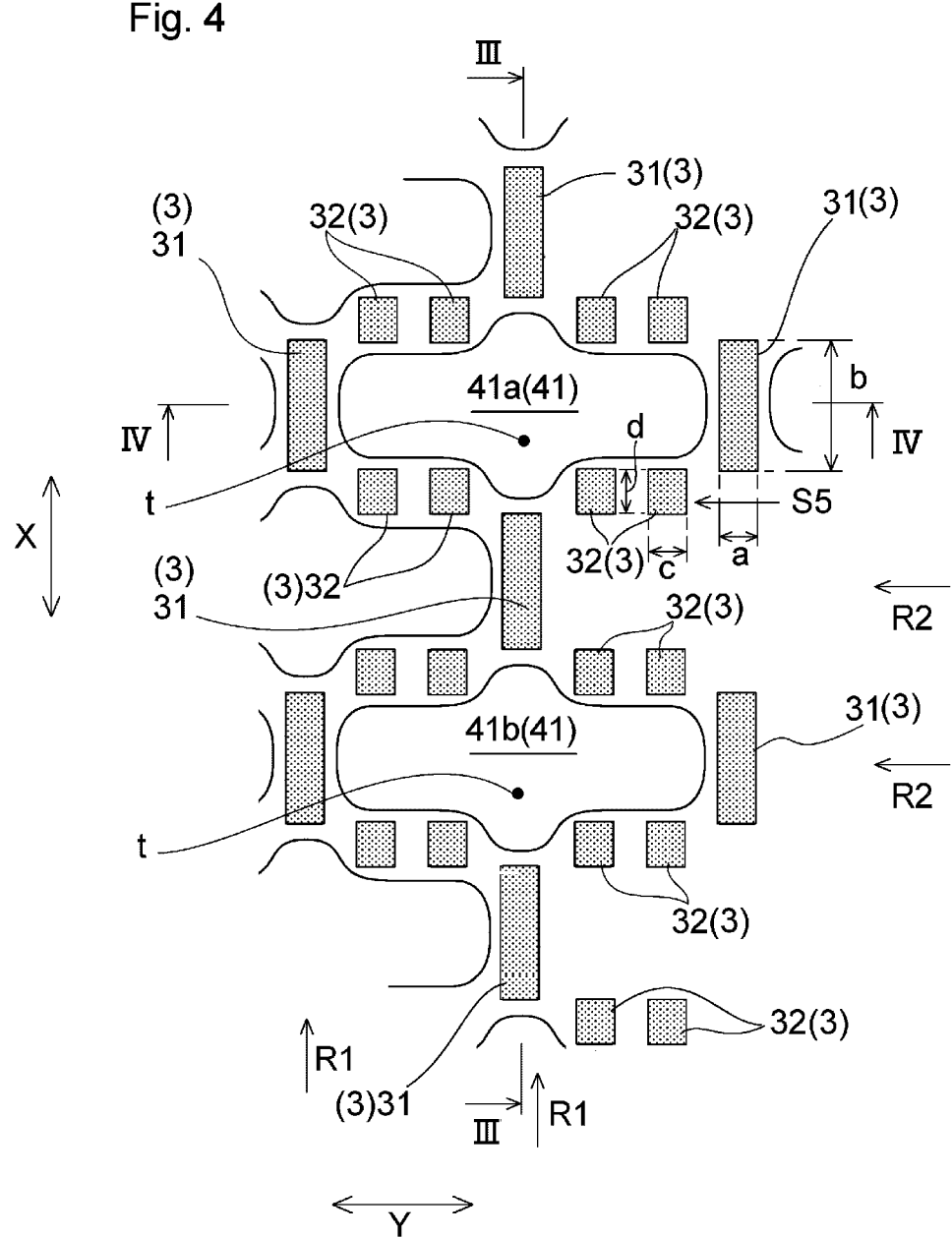
FIG. 4 is an enlarged plan view illustrating, under magnification, a portion of a projecting-and-depressed region P of the composite sheet illustrated in FIG. 3.

As illustrated in FIGS. 4 and 5, the slanting projection 41 in the present embodiment has a planar-view shape that is oblong in the lateral direction, wherein the length L1 of the slanting projection in the width direction Y of the absorbent article is longer than the length L2 thereof in the longitudinal direction X. Providing each of the slanting projections 41 with a laterally-oblong planar-view shape makes the slanting projections 41 easy to tilt so as to cover the excrement U when the projections are pressurized by the wearer's skin 7, thus further facilitating achievement of one or more of the aforementioned effects, for example. It is preferable that the length L1, in the width direction Y, of the slanting projection 41 is preferably 1.1 times or greater, more preferably 1.5 times or greater, the length L2 thereof in the longitudinal direction X, and preferably 6.0 times or less, more preferably 4.0 times or less, and preferably from 1.1 to 6.0 times, more preferably from 1.5 to 4.0 times, the length L2 thereof in the longitudinal direction.

From the viewpoint of controlling diffusion of excrement in the longitudinal direction, it is preferable that the length L1, in the width direction Y, of the slanting projection 41 is preferably 3 mm or greater, more preferably 5 mm or greater, and preferably 100 mm or less, more preferably 75 mm or less, and preferably from 3 to 100 mm, more preferably from 5 to 75 mm.

In the projecting-and-depressed region P of the present embodiment, a first sheet 1 and a second sheet 2, which are layered on one another, are joined together at a plurality of joined portions 3, and the first sheet 1 forms the slanting projections 41 that project in a direction separating from the second sheet 2 at sections other than the joined portions 3.

In this way, the three-dimensional shape of the slanting projections 41 formed by the first sheet 1 can be maintained stably. Further, since the vicinities of the rising base ends of each slanting projection 41 are fixed to the second sheet 2, each slanting projection 41 can tilt easily by employing the vicinity of the rising base end as a pivot. It is also possible to prevent the shape of the slanting projections 41 from collapsing while the absorbent article is worn, which would otherwise inhibit the achievement of the aforementioned effects. Thus, achievement of one or more of the aforementioned effects is further facilitated. In the composite sheet 10 constituting the projecting-and-depressed region P of the topsheet 12 in the present embodiment, as illustrated in FIG. 5, the surface on the second sheet 2 side is substantially flat, and projections and depressions with large undulations are formed on the first sheet 1 side by the slanting projections 41 and the depressions 30 between the slanting projections.

From the same viewpoint, it is preferable that, as illustrated in FIGS. 3 and 4, the topsheet 12 includes, in the projecting-and-depressed region P, projection rows R1 wherein a plurality of the slanting projections—whose position of the apex t is deviated toward the same side in the longitudinal direction X—are lined up along the longitudinal direction X. It is also preferable that sections 31, 32 densified by embossing are partially provided between adjacent slanting projections 41, 41 in each projection row R1.

In the present embodiment, the sections 31, 32 densified by embossing include: first joined portions 31 formed by fusion-bonding the first sheet 1 and the second sheet 2 by heat-embossing; and second joined portions 32 formed by fusion-bonding the first sheet 1 and the second sheet 2 also by heat-embossing.

For the fiber sheet forming the slanting projections 41, such as the first sheet 1 of the composite sheet 10 in the present embodiment, it is possible to use, for example, a nonwoven fabric, a woven fabric, or a knitted fabric, and preferably a nonwoven fabric. For the second sheet 2 forming the composite sheet 10 by being partially joined with the first sheet 1, it is possible to use, for example, a sheet material made of one of various materials, such as a fiber sheet—e.g., a nonwoven fabric, a woven fabric, or a knitted fabric—or a film. The sheet materials constituting the first sheet 1 and the second sheet 2 may be of the same type, or may be different from one another. The sheet material constituting the second sheet 2 may be a mesh, for example.

In cases of using a nonwoven fabric as the sheet material constituting the first sheet 1 or the second sheet 2, examples of the nonwoven fabric include air-through nonwoven fabric, spun-bonded nonwoven fabric, spun-laced nonwoven fabric, melt-blown nonwoven fabric, resin-bonded nonwoven fabric, and needle-punched nonwoven fabric. It is also possible to use a laminate made by using two or more types of the aforementioned nonwoven fabrics in combination, or a laminate made by using the aforementioned nonwoven fabric(s) and a film in combination. Among the above, it is preferable to use an air-through nonwoven fabric or a spun-bonded nonwoven fabric. The basis weight of the nonwoven fabric used as the sheet material constituting the first sheet 1 and the second sheet 2 is preferably 10 $g/m^2$ or greater, more preferably 15 $g/m^2$ or greater, and preferably 40 $g/m^2$ or less, more preferably 35 $g/m^2$ or less. The basis weight of the nonwoven fabric is preferably from 10 to 40 $g/m^2$, more preferably from 15 to 35 $g/m^2$.

For the fiber constituting the nonwoven fabric, it is possible to use fiber made of one or more of various types of thermoplastic resins. Examples of thermoplastic resins include polyolefins such as polyethylene and polypropylene, polyesters such as polyethylene terephthalate, polyamides such as nylon 6 and nylon 66, polyacrylates, polyalkyl methacrylate esters, polyvinyl chloride, and polyvinylidene chloride. One type of the aforementioned resin may be used singly, or two or more types may be used as a blend. It is also possible to use a conjugate fiber, such as a core-sheath or side-by-side conjugate fiber.

The projecting-and-depressed region P of the topsheet 12 in the present embodiment is described in further detail. As illustrated in FIG. 4, in the projecting-and-depressed region P, slanting projections 41, each being oblong in the lateral direction in a planar view, are formed as slanting projections 41 in a dispersed state in the longitudinal direction X and the width direction Y. More specifically, as illustrated in FIG. 3, the slanting projections 41 are arranged in a staggered pattern, wherein a plurality of longitudinal-direction projection rows R1—in each of which a plurality of the slanting projections 41 are arranged in a line along the longitudinal direction X at given intervals—are formed in the width direction Y. In longitudinal-direction projection rows R1 adjacent to one another in the width direction Y, the respective slanting projections 41 are arranged at positions misaligned from one another by half-pitch in the longitudinal direction X. The respective slanting projections 41 in the longitudinal-direction projection rows R1 adjacent to one another in the width direction Y partially overlap one another so as to be arranged alternately in the longitudinal direction X. With this arrangement, a barrier is created by the slanting projections 41 over the entire region in the width direction Y, and thus, diffusion of excrement in the longitudinal direction can be suppressed effectively.

Further, in the projecting-and-depressed region P, a plurality of width-direction projection rows R2—in each of which a plurality of the slanting projections 41 are arranged in a line along the width direction Y at given intervals—are formed in the longitudinal direction X.

As illustrated in FIG. 4, a longitudinally-oblong first joined portion 31 is formed between slanting projections 41 that are adjacent to one another in the longitudinal direction X in each longitudinal-direction projection row R1, wherein the length b, in the longitudinal direction X, of the first joined portion 31 is longer than the length a thereof in the width direction Y. Each first joined portion 31 is located between slanting projections 41 adjacent to one another in the width direction Y in each width-direction projection row R2. The first joined portion 31 between slanting projections 41 adjacent to one another in the width direction Y is a first joined portion 31 located between slanting projections 41 in longitudinal-direction projection rows R1 adjacent to one another in the width direction. The length b, in the longitudinal direction X, of the longitudinally-oblong first joined portion 31 is preferably 1.2 times or greater, more preferably 1.5 times or greater, the length a thereof in the width direction Y, and preferably 5.0 times or less, more preferably 3.0 times or less, the length a thereof, and preferably from 1.2 to 5.0 times, more preferably from 1.5 to 3.0 times, the length a thereof.

The periphery of each of the slanting projections 41 is surrounded by the first joined portions 31 and second joined portions 32 each having a shorter length, in the longitudinal direction, than the first joined portion 31. The periphery of each slanting projection 41 is surrounded by four or more joined portions 3, and thereby, a depression 30 is formed surrounding each slanting projection 41. The depressions 30 surrounding the respective slanting projections 41 are continuous, thereby forming a continuous depression that is continuous in a mesh form in sections other than the slanting projections 41 in the projecting-and-depressed region P.

When the joined portions between the first sheet 1 and the second sheet 2 are collectively referred to as joined portions 3, the number of joined portions 3 surrounding each slanting projection 41 is preferably 4 or greater, more preferably 8 or greater, and preferably 20 or fewer, more preferably 16 or fewer. It is preferable that the joined portions 3, provided in the aforementioned number, are provided as a pair of joined portions sandwiching each slanting projection 41 from both sides in the longitudinal direction X, or as a pair of joined portions sandwiching each slanting projection 41 from both sides in the width direction Y.

The length d, in the longitudinal direction X, of the second joined portion 32 is preferably from 20 to 85%, more preferably from 30 to 70%, of the length b, in the longitudinal direction, of the first joined portion 31. The length c, in the width direction Y, of the second joined portion 32 is preferably from 0.8 to 1.2 times, more preferably from 0.9 to 1.1 times, the length a, in the width direction Y, of the first joined portion 31.

It is preferable that densified portions, where the first sheet (sheet material) forming the slanting projections 41 is partially densified, are provided between the slanting projections 41 that are adjacent to one another in the longitudinal direction X, such as between the slanting projections 41 included in the same longitudinal-direction projection row R1. In cases where the slanting projections 41 are formed by the composite sheet 10 including joined portions 3 between the first sheet 1 and the second sheet 2 as in the present embodiment, it is preferable that the joined portions are portions formed by partially pressurizing and densifying the sheet by embossing, for example. In cases where a single-layer sheet material is partially pressurized and compressed, or the joined portions 3 between the first sheet 1 and the second sheet 2 are partially pressurized and compressed by embossing etc., the pressurized/compressed sections serve as densified portions having a higher density than other sections. This is preferable because each of the slanting projections 41 can easily be tilted, by employing the vicinity of the end of the respective densified portion as a base point, so as to cover a wide area over the excrement U inside the depressions 30.

Further, from the same viewpoint, it is further preferable that, in each densified portion formed between the slanting projections 41, the density of the end 3b on the opposite side (rear side or front side) from the one side (front side or rear side), toward which the position of the slanting projection 41's apex t is deviated, is higher than the density of the end 3a on the one side.

The density of the one-side end 3a and the other-side end 3b of the densified portion is measured as follows.

{Method for Measuring Density of Ends of Densified Portion}

The density of the ends of the densified portion can be found as follows. A 1.0×1.0-mm measurement piece is cut out from each of both ends, in the longitudinal direction X, of the densified portion. The volume ($mm^3$) of the measurement piece is calculated by multiplying the planar area, 1.0 $mm^2$, of the measurement piece by the thickness of the measurement piece, and the volume ($mm^3$) is converted to $cm^3$. Then, the weight (g) of the measurement piece is divided by the volume ($cm^3$), to thereby obtain the density. The weight of the measurement piece is found by: collectively weighing, with a balance scale, five or more measurement pieces cut out from each of both ends of the densified portion; and employing the mean value found by dividing the total weight by the number of measurement pieces. The thickness of the measurement piece is a value found by: cutting, along the width direction Y, the sheet at respective positions separated by 0.5 mm, in the longitudinal direction X, from the respective ends of the densified portion in the longitudinal direction X with a sharp edged tool; observing the respective cross sections with a digital microscope (from Keyence Corporation); and measuring the distance from the lower surface of the densified portion to the upper surface at each cross section's center portion in the width direction. The thickness is the mean value found from the measurements of at least five test pieces for each of both ends of the densified portion.

From the viewpoint of achieving one or more of the aforementioned effects more reliably, it is preferable that the height H1 of each slanting projection 41 (see FIG. 5(a)) is preferably 1.0 mm or greater, more preferably 2.0 mm or greater, and preferably 5.0 mm or less, more preferably 4.0 mm or less, and preferably from 1.0 to 5.0 mm, more preferably from 2.0 to 4.0 mm. In cases where the projecting-and-depressed region P also includes non-slanting projections, the height of each non-slanting projection may be the same as, or different from, the height of the slanting projection 41, and for example, is slightly lower than the slanting projection 41, taking into account the slanting. The preferred range for the height of the non-slanting projection is the same as the aforementioned preferred range for the height of the slanting projection.

In cases where the projecting-and-depressed region P is formed by the composite sheet 10 including the joined portions 3 between the first sheet 1 and the second sheet 2, the height of each slanting projection 41 is defined as the distance from the lower surface of the second sheet 2 to the upper surface of the first sheet 1, as illustrated in FIG. 5. The height is the value found by observing the cross section of a single projection by using a digital microscope (from Keyence Corporation), and measuring the shortest distance between the lower surface of the second sheet 2 and the apex of the projection.

In cases where the projecting-and-depressed region P is formed from a single-layer sheet material, the height of each slanting projection is the height difference between: a straight line connecting the respective apexes of slanting projections adjacent to one another in the longitudinal direction X; and the lower surface in a section located between the slanting projections and farthest from the straight line.

The position of the apex t of the slanting projection 41, the height of the slanting projection 41, and the like are determined by observing a cross section passing through the apex t of the slanting projection 41 and extending in the longitudinal direction X. In cases where the slanting projections 41 are formed by a sheet material (first sheet) joined to another sheet such as the second sheet 2, this observation is done by removing the composite sheet 10, which includes joined portions 3 between the first sheet 1 and the second sheet 2, from the absorbent article and observing a cross section passing through the apex t of the slanting projection 41 and extending in the longitudinal direction X.

The composite sheet 10 including the projecting-and-depressed region P in which the slanting projections 41 are formed can be manufactured according to a method similar to the method described in JP 2015-112343A. That is, a continuous first sheet 1 is supplied between a first roller and a second roller whose respective circumferential surfaces have intermeshing shapes, thereby deforming the first sheet 1 into a projecting-and-depressed shape, and then, the first sheet 1 is moved away from the intermeshing section while keeping the sheet along the circumferential surface portion of the first roller. Then, a second sheet 2 is supplied onto the first sheet 1, and the two sheets 1, 2 are partially joined together by being sandwiched and pressurized, while being heated, between the projections of the first roller and a heat roller.

Next, the obtained composite sheet is pressurized between first nip rollers, and at that time, the composite sheet is pressurized while being pulled strongly toward the downstream side by, for example, second nip rollers arranged downstream of the first nip rollers. In this way, the projections formed on the composite sheet are slanted toward the upstream side, and thus, it is possible to obtain a composite sheet 10 including a projecting-and-depressed region P having slanting projections 41 formed thereon. From the viewpoint of forming the slanting projections 41, it is preferable that the circumferential velocity of the second nip rollers is faster than the circumferential velocity of the first nip rollers, and is preferably at least 1.05 times, more preferably at least 1.1 times, the circumferential velocity of the first nip rollers. It is also preferable to heat at least the roller, among the first nip rollers, on the side contacting the first sheet 1 to a temperature below the melting point of constituent fibers primarily constituting the first sheet 1—for example, to a temperature within a range from 50° C. below the melting point to a temperature below the melting point.

Further, in order to form densified portions (joined portions 3) having different densities between both ends in the longitudinal direction X, it is possible to use, as the first roller, a roller having projections whose height, from the roller's base surface to the tip-end surface, changes continuously or stepwise along the roller's circumferential direction, and sandwich and pressurize the sheet between such a first roller and a heat roller to form the joined portions 3 such as the first joined portions 31 and the second joined portions 32.

As illustrated in FIG. 3, the composite sheet 10 employed in the disposable diaper 100 of the first embodiment includes a central region M as the projecting-and-depressed region P, and side regions S, S located on both sides of the central region M, wherein the side regions S, S include non-slanting projections 43 in each of which the position of the apex t is present at the central position 43c located between both ends of the projection. In order to manufacture the composite sheet 10 having the aforementioned configuration, the projecting-and-depressed shapes of the first roller and the second roller, as well as the patterns of the joined portions formed by the first roller and the heat roller, may be made different between the central portion and the lateral side portions of the first sheet, and only the central portion of the obtained composite sheet may be subjected to the treatment by the aforementioned first nip rollers.

Next, a second embodiment of an absorbent article of the present invention is described with reference to FIG. 8. As for the diaper according to the following second embodiment, only features that are different from those of the diaper of the first embodiment will be described. Features that are not particularly described are the same as those of the diaper of the first embodiment, and explanation on the foregoing diaper is applied as appropriate.

Figure 8A:
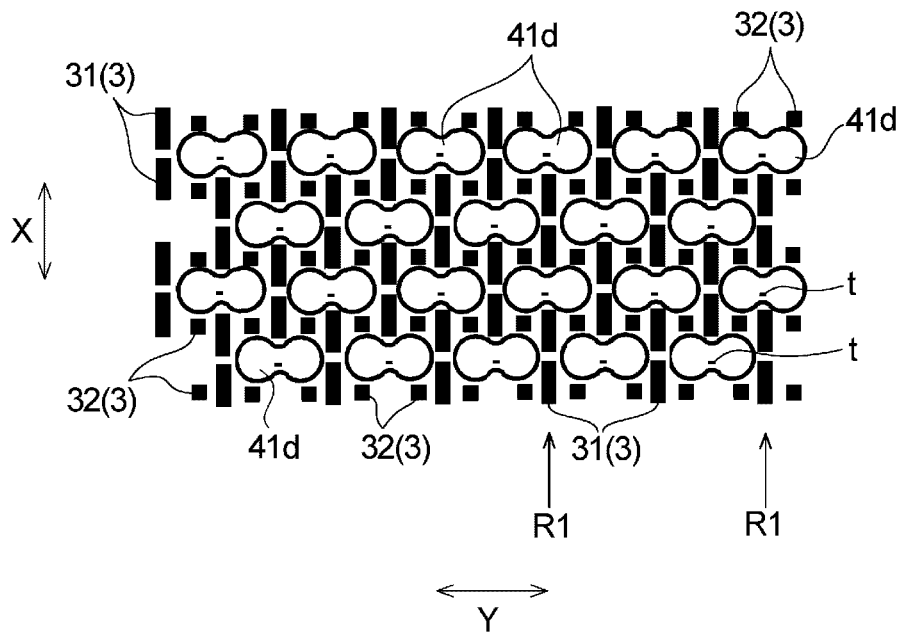
FIG. 8(*a*) is an enlarged plan view illustrating, under magnification, a portion of a projecting-and-depressed region of a topsheet (composite sheet) according to a second embodiment, and FIG. 8(*b*) is an enlarged view of a slanting projection.
Figure 8B:
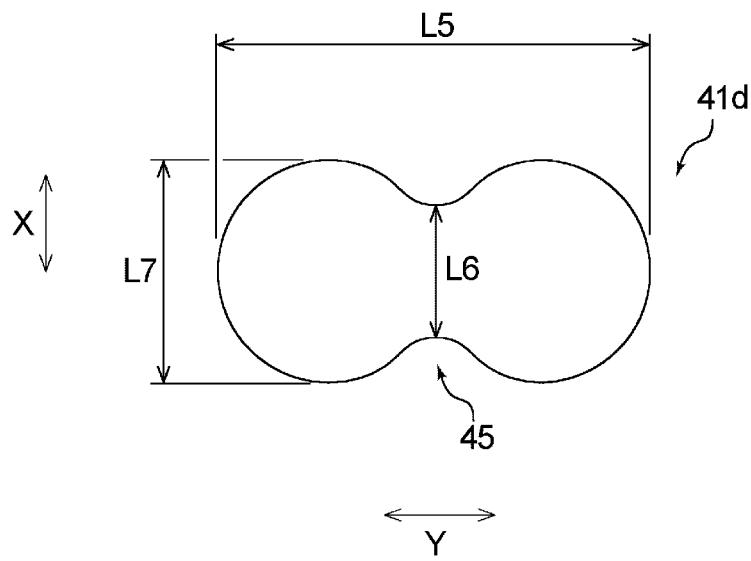

FIG. 8(*a*) is a diagram illustrating a portion of a projecting-and-depressed region of a topsheet 12 according to the second embodiment. The topsheet in the second embodiment is constituted by a composite sheet, and includes a projecting-and-depressed region in which slanting projections 41*d* are formed in a dispersed state in the longitudinal direction X and the width direction Y according to a predetermined pattern. In the composite sheet of the second embodiment, the slanting projections 41*d* are formed uniformly according to the pattern illustrated in FIG. 8(*a*), and the sheet does not include a central region M and side regions S as in the first embodiment.

The composite sheet of the second embodiment includes the projecting-and-depressed region over the entire region thereof. Further, the projecting-and-depressed region includes slanting projections 41*d* having a planar-view shape that is different from that in the composite sheet 10 of the first embodiment. As illustrated in FIG. 8(*b*), the slanting projection 41*d* in the projecting-and-depressed region has a planar-view shape that is oblong in the lateral direction wherein the length L5 thereof in the width direction Y of the absorbent article is longer than the length L7 in the longitudinal direction X, and has, in a central portion in the width direction Y, a narrowed portion 45 where the length in the longitudinal direction X is made shorter compared to the sections located on both sides thereof. The length L5 of the slanting projection 41*d* in the width direction Y is the maximum length of the slanting projection 41*d* in the width direction Y, and the length L7 in the longitudinal direction X is the maximum length of the slanting projection 41*d* in the longitudinal direction X. The composite sheet, including such slanting projections 41*d*, can capture excrement U in the respective narrowed portions 45 of the slanting projections 41*d*. This further improves the effect of controlling diffusion of excrement U, in combination with the effect of controlling diffusion of excrement U achieved by the slanting of the rising section g (see FIG. 5) of each of the slanting projections 41*d*.

From the viewpoint of effectively capturing excrement U, it is preferable that the length L5, in the width direction Y, of the slanting projection 41*d* (see FIG. 8(*b*)) is preferably 1.5 times or greater, more preferably 2.0 times or greater, the length L6, in the longitudinal direction X, of the narrowed portion 45 (see FIG. 8(*b*)), and preferably 8.0 times or less, more preferably 6.0 times or less, the length L6 of the narrowed portion, and preferably from 1.5 to 8.0 times, more preferably from 2.0 to 6.0 times, the length L6 of the narrowed portion.

The present invention has been described above according to preferred embodiments thereof, but the present invention is not limited to the foregoing embodiments and may be modified as appropriate.

For example, the composite sheet 10 used for the topsheet 12 does not have to include side regions S, S having projections formed according to a pattern different from that in the central region M. Instead, a composite sheet 10 whose entire region has the same configuration as the central region M may be used for the topsheet 12.

In the foregoing first embodiment, as illustrated in FIG. 3, the projecting-and-depressed region P including the slanting projections 41 is formed over the entire length, in the longitudinal direction, of the diaper 100. In the absorbent article of the present invention, however, the projecting-and-depressed region P including the slanting projections 41 only needs to be formed in one of the portions, in the longitudinal direction, of the absorbent article, and for example, it may be formed only in the front portion A, only in the rear portion B, or only in the crotch portion C, or may be formed only in the crotch portion C and the front portion A or only in the crotch portion C and the rear portion B.

The absorbent article of the present invention may include, in the projecting-and-depressed region, a region including a plurality of the slanting projections whose position of the apex t is deviated toward the same side in the longitudinal direction X. This region is also referred to as an identically-slanting region. For example, in cases where there is a region wherein a plurality of forward slanting projections are formed in the rear portion B, this region is an identically-slanting region.

Figure 9A:
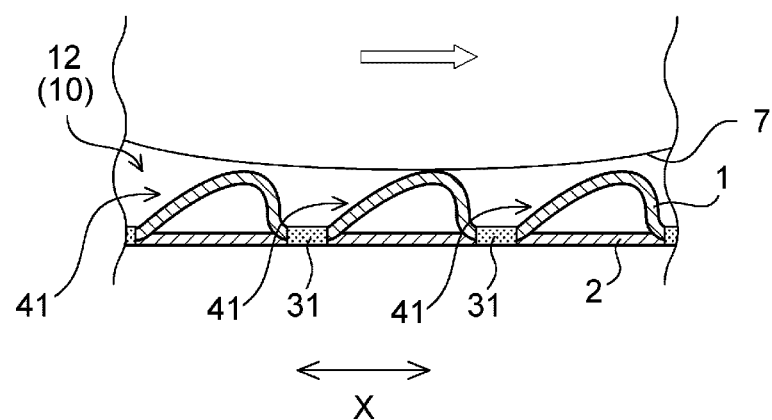
FIG. 9 shows diagrams illustrating effects of slanting projections in an identically-slanting region, wherein FIG. 9(*a*) is a diagram illustrating actions/operations when friction is caused along the slanting direction of the slanting projections, and FIG. 9(*b*) is a diagram illustrating actions/operations when friction is caused in a direction opposite from the slanting direction.
Figure 9B:
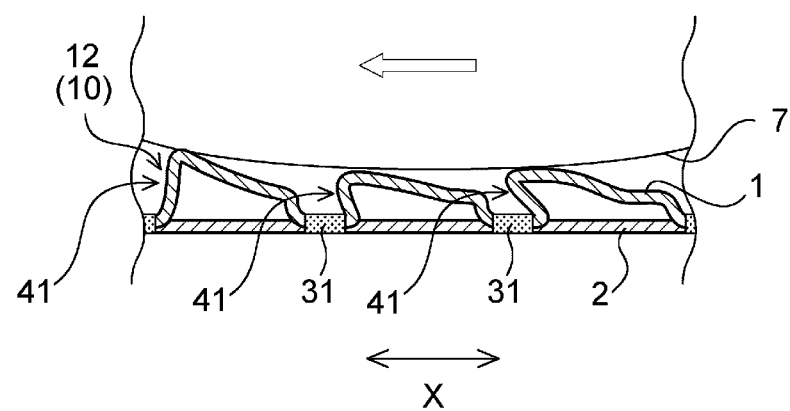

In the identically-slanting region, it is preferable that the mean deviation MMD1 of frictional coefficient, in the slanting direction, of the plurality of slanting projections is different from the mean deviation MMD2 of frictional coefficient thereof in the opposite direction from the slanting direction, and it is more preferable that the mean deviation MMD1 of frictional coefficient, in the slanting direction, of the plurality of slanting projections is smaller than the mean deviation MMD2 of frictional coefficient thereof in the opposite direction from the slanting direction. This configuration can reduce friction force when the skin comes into contact along the slanting direction in the identically-slanting region, while increasing friction force when the skin comes into contact along the opposite direction. Thus, it is possible to control the direction of movement of the topsheet by contact with the skin. To describe this effect in more detail, an example will be explained below, wherein the rear portion B includes an identically-slanting region including a plurality of forward slanting projections, and the front portion A includes an identically-slanting region including a plurality of rearward slanting projections. In this example, when putting on the diaper, the skin 7 and the slanting projections 41 come into contact along the slanting direction of the forward slanting projections and the rearward slanting projections (see FIG. 9(a)). Thus, friction force (resistance) between the skin and the slanting projections can be reduced, and the task of putting on the diaper can be performed easily. Further, in a worn state, i.e., in a state where the skin 7 and the slanting projections are in contact with one another, when a force is applied toward the opposite direction from the slanting direction of the slanting projections, the slanting projections deform, thereby increasing friction force (see FIG. 9(b)). This effectively suppresses the diaper, in a worn state, from moving out of position, and further suppresses the aforementioned leakage of excrement.

Friction in the slanting direction of the plurality of slanting projections in the identically-slanting region is friction that is created during movement over the plurality of slanting projections toward the side toward which the position of the apex t of each slanting projection is deviated. Friction in the opposite direction from the slanting direction is friction that is created during movement toward the opposite side from the side toward which the position of the apex is deviated. In the identically-slanting region of the rear portion B in this example, friction in the slanting direction is friction that is created along the slanting direction of the forward slanting projections, and is friction that is created during movement from the rear portion B side toward the crotch portion C side; whereas friction in the opposite direction is friction that is created during movement from the crotch portion C side toward the rear portion B side. In the identically-slanting region of the front portion A in this example, friction in the slanting direction is friction that is created along the slanting direction of the rearward slanting projections, and is friction that is created during movement from the front portion A side toward the crotch portion C side; whereas friction in the opposite direction is friction that is created during movement from the crotch portion C side toward the front portion A side. The mean deviation MMD of frictional coefficient indicates the degree of variation in frictional coefficient caused during movement along the slanting direction or the opposite direction in the following measurement method.

{Method for Measuring Mean Deviation MMD of Frictional Coefficient in Slanting Direction and Opposite Direction in Identically-Slanting Region}

The mean deviation MMD of frictional coefficient is measured using KES-FB4-AUTO-A (product name) from Kato Tech Co., Ltd. according to the method described in the following book:

Sueo Kawabata, "Standardization and Analysis of Texture Evaluation", 2nd edition, Texture Measurement and Standardization Committee, The Textile Machinery Society of Japan (Jul. 10, 1980).

First a sample that is 20 cm long in the longitudinal direction and 10 cm long in the width direction is cut out from an identically-slanting region of a topsheet. The sample is placed, with its skin-facing surface facing up, on a sample stage having a flat, smooth metal surface. The sample is reciprocated back and forth over a distance of 2 cm along the diaper's longitudinal direction at a constant speed of 0.1 cm/sec while pressing the contact surface of a contact against the skin-facing surface of the sample with a force of 49 cN, to thereby measure the respective frictional coefficients in the slanting direction and the opposite direction. The forward path and the return path of this reciprocating movement are respectively considered the movement in the slanting direction of the slanting projections and the movement in the opposite direction from the slanting direction. During this reciprocating movement, a uniaxial tension of 19.6 cN/cm is applied to the sample. The contact is made of twenty 0.5-mm-dia. piano lines arranged side by side and bent into a U-shape at a width of 10 mm. The contact surface of the contact is pressed against the sample with a force of 49 cN by using a weight. By this measurement, the mean deviation MMD of frictional coefficient in each of the slanting direction of the slanting projections and the opposite direction in the identically-slanting region is found. The measurement is repeated three times, and, for each of the slanting direction and the opposite direction, the mean value of the mean deviations MMD of frictional coefficient is calculated and is respectively considered the mean deviation $MMD_1$ of frictional coefficient in the slanting direction and the mean deviation $MMD_2$ of frictional coefficient in the opposite direction.

From the viewpoint of further facilitating the task of putting on the diaper and further effectively suppressing the diaper in a worn state from moving out of position, it is preferable that, on the precondition that the mean deviation $MMD_1$ of frictional coefficient in the slanting direction is smaller than the mean deviation $MMD_2$ of frictional coefficient in the opposite direction ($MMD_2 > MMD_1$), the difference between the mean deviation $MMD_1$ of frictional coefficient in the slanting direction in the identically-slanting region and the mean deviation $MMD_2$ of frictional coefficient in the opposite direction is preferably 0.001 or greater, more preferably 0.002 or greater, and preferably 0.02 or less, more preferably 0.01 or less, and preferably from 0.001 to 0.02, more preferably from 0.002 to 0.01.

The topsheet 12 includes an identically-slanting region preferably in at least the rear portion B, and more preferably in both the rear portion B and the front portion A, and the respective mean deviations MMD of frictional coefficients in the slanting direction and the opposite direction in the identically-slanting region satisfy the aforementioned relationship ($MMD_2 > MMD_1$). In cases where only the rear portion B includes the identically-slanting region and the aforementioned relationship ($MMD_2 > MMD_1$) is satisfied, it is preferable that there is no difference between the respective mean deviations MMD of frictional coefficients in the slanting direction and the opposite direction in the front portion A.

Further, slanting projections and non-slanting projections may coexist in the projecting-and-depressed region P. The projections may coexist by being present in a mixed state. Note, however, that it is preferable that the projecting-and-depressed region includes at least one section, preferably a plurality of sections, in which two or more slanting projections (forward slanting projections or rearward slanting projections) whose position of the apex is deviated in the same direction are lined up along the longitudinal direction X. Further, projection rows including a plurality of forward slanting projections or rearward slanting projections lined up in the longitudinal direction X and projection rows including a plurality of non-slanting projections lined up in the longitudinal direction X may be formed, and these projection rows may be formed alternately in the width direction Y of the absorbent article, or formed according to a suitable order.

The number of slanting projections in the projecting-and-depressed region P to the number of all of the projections in the projecting-and-depressed region P is preferably 30% or greater, more preferably 50% or greater, and preferably 100% or less, more preferably 90% or less, and preferably from 30 to 100%, more preferably from 50 to 90%.

The rate of the number of slanting projections to the number of all projections in the projecting-and-depressed region P, i.e., the rate of the slanting projections, is a mean value of rates of slanting projections in five or more measurement pieces. The rate of slanting projections of the measurement pieces is found by: cutting out five or more 50×50-mm measurement pieces from the projecting-and-depressed region P; finding the number of all projections present in the measurement pieces; finding the number of slanting projections by observing the respective cross section passing through the apex of each projection and extending along the longitudinal direction X; and dividing the number of slanting projections by the number of all projections present in the measurement pieces.

In the projecting-and-depressed region P, the width-direction projection row, in which a plurality of projections 4 are lined up along the width direction Y, may be constituted only by slanting projections, or may include slanting projections and non-slanting projections. The projecting-and-depressed region P may include width-direction projection rows having mutually different rates of the number of slanting projections.

From the viewpoint of suppressing diffusion of feces in the longitudinal direction X, it is preferable that the projecting-and-depressed region P includes, as the width-direction projection row, a high-rate slanting projection row in which the slanting projections account for half or more of the projections constituting the width-direction projection row. In the high-rate width-direction projection row, the slanting projections account for at least half, preferably more than half, more preferably 60% or greater, even more preferably 80% or greater, further more preferably 100%, of the projections. From the viewpoint of further suppressing diffusion of feces, it is preferable that the projecting-and-depressed region P includes a plurality of the high-rate slanting projection rows. A plurality of high-rate slanting projection rows may be included in such a manner that, for example, the high-rate slanting projection rows cover the entire region of the projecting-and-depressed region P, or high-rate slanting projection rows and non-high-rate slanting projection rows are provided according to a discretionary pattern lined up alternately in the longitudinal direction X. As regards the width-direction projection row, the non-high-rate slanting projection row may either be a low-rate slanting projection row in which the rate of the slanting projections is low, or a non-slanting projection row including only non-slanting projections. An example of a discretionary pattern may be a pattern wherein two non-high-rate slanting projection rows and one high-rate slanting projection row are lined up alternately along the longitudinal direction X. In cases where the high-rate slanting projection row includes slanting projections and non-slanting projections, it is preferable that, in the high-rate slanting projection row, small slanting-projection rows, each including a plurality of slanting projections continuously lined up in the width direction Y, and non-slanting projections are lined up alternately in the width direction Y.

As illustrated in FIG. 1, in cases where the topsheet includes a central region M and side regions S, S and the patterns according to which the projections are formed are different between the central region M and the side regions S, S, the rate of slanting projections in the projecting-and-depressed region P and the rate of slanting projections in each width-direction projection row are measured in the central region M.

The shapes and arrangements of the joined portions 3 surrounding the respective slanting projections 41, as well as other joined portions, can be determined as appropriate. Other than rectangular and square, each of the joined portions may have discretionary shapes, such as circular, elliptic, oval, triangular, quadrangular, pentagonal, hexagonal, star-shaped, or heart-shaped.

The absorbent article of the present invention may be an underpants-type (pull-on-type) disposable diaper instead of an open-type disposable diaper, or may be a pull-on sanitary napkin, a normal non-pull-on sanitary napkin, an incontinence pad, a pantiliner, or the like.

The present invention further recites the absorbent article related to the embodiments described above.

[1] An absorbent article comprising a topsheet including a projecting-and-depressed region, a backsheet, and an absorbent member arranged between the topsheet and the backsheet, the absorbent article having a longitudinal direction that corresponds to a front-rear direction of a wearer and a width direction that is orthogonal to the longitudinal direction, wherein:
 a plurality of slanting projections are formed in the projecting-and-depressed region;
 the slanting projections project toward the wearer's skin side, and a position of an apex of each of the slanting projections is deviated toward one side in the longitudinal direction from a central position located between both ends of the slanting projection in the longitudinal direction.

[2] The absorbent article as set forth in clause [1], wherein the slanting projection is slanted in a state in which a rising section of the slanting projection on the one side, toward which the position of the apex is deviated, is tilted more toward the one side than perpendicular.

[3] The absorbent article as set forth in clause [1] or [2], wherein the slanting projection includes an overhanging section on the one side toward which the position of the apex is deviated.

[4] The absorbent article as set forth in any one of clauses [1] to [3], wherein the position of the apex of the slanting projection does not go beyond a position of another slanting projection's end that is located on an opposite side from the one side, the another slanting projection being adjacent to the slanting projection on the one side toward which the position of the apex is deviated.

[5] The absorbent article as set forth in any one of clauses [1] to [4], wherein, when a slanting angle perpendicular to a plane extending parallel to a surface of the topsheet is defined as 90°, the slanting angle of the rising section of the slanting projection is less than 90°, preferably 30° or greater and less than 80°, more preferably from 45° to 60°.

[6] The absorbent article as set forth in any one of clauses [1] to [5], wherein, when a length between the both ends, in the longitudinal direction, of the slanting projection 41 is defined as 100%, the position of the apex of the slanting projection is located outside a range covering a distance of 5% in front and rear of the central position, and is preferably located outside a range covering a distance of 10% in front and rear of the central position.

[7] The absorbent article as set forth in any one of clauses [1] to [6], wherein the slanting projection has a laterally-oblong planar-view shape in which a length, in the width direction, of the slanting projection is longer than a length thereof in the longitudinal direction.

[8] The absorbent article as set forth in any one of clauses [1] to [7], wherein the length L1, in the width direction, of the slanting projection is 1.1 times or greater, preferably 1.5 times or greater, 6.0 times or less, preferably 4.0 times or less, and from 1.1 to 6.0 times, preferably from 1.5 to 4.0 times the length L2 thereof in the longitudinal direction.

[9] The absorbent article as set forth in any one of clauses [1] to [8], wherein the length L1, in the width direction, of the slanting projection is 3 mm or greater, preferably 5 mm or greater, and 100 mm or less, preferably 75 mm or less, and from 3 to 100 mm, preferably from 5 to 75 mm.

[10] The absorbent article as set forth in any one of clauses [1] to [9], wherein a height H1 of the slanting projection is 1.0 mm or greater, preferably 2.0 mm or greater, and 5.0 mm or less, preferably 4.0 mm or less, and from 1.0 to 5.0 mm, preferably from 2.0 to 4.0 mm.

[11] The absorbent article as set forth in any one of clauses [1] to [10], wherein:
 the projecting-and-depressed region includes non-slanting projections in addition to the slanting projections; and
 the non-slanting projections project toward the wearer's skin side, and the position of the apex of each of the non-slanting projections is present at the central position located between both ends, in the longitudinal direction, of the non-slanting projection.

[12] The absorbent article as set forth in any one of clauses [1] to [11], wherein the number of slanting projections in the projecting-and-depressed region to the number of all projections in the projecting-and-depressed region is 30% or greater, preferably 50% or greater, and 100% or less, preferably 90% or less, and from 30 to 100%, preferably from 50 to 90%.

[13] The absorbent article as set forth in any one of clauses [1] to [12], wherein the slanting projections comprises only either forward slanting projections or rearward slanting projections over the entire topsheet or over an entire central region located in a central area, in the width direction, of the topsheet,
 a position of the apex of each of the forward slanting projections is deviated toward the front side from the central position between the both ends, and
 a position of the apex of each of the rearward slanting projections is deviated toward the rear side from the central position.

[14] The absorbent article as set forth in any one of clauses [1] to [13], wherein:
 the projecting-and-depressed region includes a projection row in which a plurality of the slanting projections whose position of the apex is deviated toward the same side in the longitudinal direction are lined up along the longitudinal direction; and
 a depression including a densified portion is provided between the slanting projections in the projection row.

[15] The absorbent article as set forth in any one of clauses [1] to [14], wherein, in the projecting-and-depressed region, a first sheet and a second sheet which are layered on one another are joined together at a plurality of joined portions, and the first sheet forms the slanting projections that project in a direction separating from the second sheet at sections other than the joined portions.

[16] The absorbent article as set forth in clause [15], wherein a surface on the second sheet side is substantially flat, and projections and depressions having large undulations are formed on the first sheet side by the slanting projections and depressions located between the slanting projections.

[17] The absorbent article as set forth in clause [15] or [16], wherein:
 the topsheet includes, as densified portions in the projecting-and-depressed region,
  first joined portions formed by fusion-bonding the first sheet and the second sheet by embossing, and
  second joined portions formed by fusion-bonding the first sheet and the second sheet by embossing;
 in the projecting-and-depressed region,
  a plurality of width-direction projection rows, in each of which a plurality of the slanting projections are arranged in a line along the width direction at given intervals, are formed in the longitudinal direction, and
  a plurality of projection rows, in each of which a plurality of the slanting projections are arranged in a line along the longitudinal direction at given intervals, are formed in the width direction;

the first joined portion between the slanting projections that are adjacent to one another in the longitudinal direction in each of the projection rows is located between the slanting projections adjacent to one another in the width direction in each of the width-direction projection rows; and the first joined portion between the slanting projections adjacent to one another in the width direction is located between the slanting projections in the projection rows adjacent to one another in the width direction.

[18] The absorbent article as set forth in clause [17], wherein a length b, in the longitudinal direction, of the first joined portion is 1.2 times or greater, preferably 1.5 times or greater, 5.0 times or less, preferably 3.0 times or less, and from 1.2 to 5.0 times, more preferably from 1.5 to 3.0 times, the length a thereof a length, in the width direction, of the first joined portion.

[19] The absorbent article as set forth in clause [17] or [18], wherein a periphery of each of the slanting projections is surrounded by the first joined portions and the second joined portions each having a shorter length, in the longitudinal direction, than the first joined portion.

[20] The absorbent article as set forth in any one of clauses [17] to [19], wherein a length d, in the longitudinal direction X, of the second joined portion is from 20 to 85%, preferably from 30 to 70%, of the length b, in the longitudinal direction, of the first joined portion.

[21] The absorbent article as set forth in any one of clauses [17] to [20], wherein a length c, in the width direction, of the second joined portion is from 0.8 to 1.2 times, preferably from 0.9 to 1.1 times the length a, in the width direction, of the first joined portion.

[22] The absorbent article as set forth in any one of clauses [17] to [21], wherein the densified portion's density on the opposite side from the one side, toward which the position of the apex is deviated, is higher than the density thereof on the one side.

[23] The absorbent article as set forth in any one of clauses [1] to [22], wherein the projecting-and-depressed region includes a width-direction projection row in which a plurality of projections are lined up along the width direction, and includes, as the width-direction projection row, a high-rate slanting projection row in which the slanting projections account for half or more of the projections constituting the width-direction projection row.

[24] The absorbent article as set forth in clause [23], wherein, in the width-direction projection row, the slanting projections account for more than half, preferably 60% or greater, more preferably 80% or greater, even more preferably 100%, of the projections.

[25] The absorbent article as set forth in clause [23] or [24], wherein the projecting-and-depressed region includes a plurality of the high-rate slanting projection rows.

[26] The absorbent article as set forth in any one of clauses [23] to [25], wherein:

in addition to the high-rate slanting projection row, the projecting-and-depressed region includes, as the width-direction projection row, a non-high-rate slanting projection row which is either a low-rate slanting projection row in which the rate of the slanting projections is low, or a non-slanting projection row including only non-slanting projections; and the high-rate slanting projection row and the non-high-rate slanting projection row are arranged alternately in the longitudinal direction.

[27] The absorbent article as set forth in any one of clauses [1] to [26], wherein, when the absorbent article's entire length in the longitudinal direction is divided into three equal parts and the absorbent article is divided into a rear portion to be arranged on the wearer's rear side, a front portion to be arranged on the wearer's front side, and a crotch portion located between the front portion and the rear portion, forward slanting projections, whose position of the apex is deviated toward the front side from the central position between the both ends, are formed as the slanting projections in the rear portion.

[28] The absorbent article as set forth in any one of clauses [1] to [27], wherein, when the absorbent article's entire length in the longitudinal direction is divided into three equal parts and the absorbent article is divided into a rear portion to be arranged on the wearer's rear side, a front portion to be arranged on the wearer's front side, and a crotch portion located between the front portion and the rear portion, rearward slanting projections, whose position of the apex is deviated toward the rear side from the central position between the both ends, are formed as the slanting projections in the front portion.

[29] The absorbent article as set forth in any one of clauses [1] to [28], wherein, in the projecting-and-depressed region, the slanting projections are formed in a dispersed state in the longitudinal direction and the width direction and are arranged in a staggered manner.

[30] The absorbent article as set forth in any one of clauses [1] to [29], wherein:

the projecting-and-depressed region includes an identically-slanting region including a plurality of the slanting projections whose position of the apex is deviated toward the same side in the longitudinal direction; and in the identically-slanting region, a mean deviation $MMD_1$ of frictional coefficient, in the slanting direction, of the plurality of slanting projections is different from a mean deviation $MMD_2$ of frictional coefficient thereof in an opposite direction from the slanting direction.

[31] The absorbent article as set forth in any one of clauses [1] to [30], wherein:

the projecting-and-depressed region includes an identically-slanting region including a plurality of the slanting projections whose position of the apex is deviated toward the same side in the longitudinal direction; and in the identically-slanting region, the mean deviation $MMD_1$ of frictional coefficient, in the slanting direction, of the plurality of slanting projections is smaller than the mean deviation $MMD_2$ of frictional coefficient thereof in the opposite direction from the slanting direction.

[32] The absorbent article as set forth in clause [30] or [31], wherein a difference between the mean deviation $MMD_1$ of frictional coefficient in the slanting direction in the identically-slanting region and the mean deviation $MMD_2$ of frictional coefficient in the opposite direction is from 0.001 to 0.02.

[33] The absorbent article as set forth in clause [30] or [31], wherein a difference between the mean deviation $MMD_1$ of frictional coefficient in the slanting direction in the identically-slanting region and the mean deviation $MMD_2$ of frictional coefficient in the opposite direction is from 0.002 to 0.01.

INDUSTRIAL APPLICABILITY

With the absorbent article of the present invention, it is easy to control the migration of excrement, and, by suppressing/controlling diffusion of excrement, it is possible to effectively improve excrement leakage preventability, etc. Further, deformation of the slanting projections, for example, can effectively create a state in which excrement remaining between the projections is less prone to adhere to the wearer's skin.

The invention claimed is:

1. An absorbent article comprising a topsheet including a projecting-and-depressed region, a backsheet, and an absorbent member arranged between the topsheet and the backsheet, the absorbent article having a longitudinal direction that corresponds to a front-rear direction of a wearer and a width direction that is orthogonal to the longitudinal direction, wherein:
   a plurality of slanting projections are formed in the projecting-and-depressed region;
   the slanting projections project toward the wearer's skin side, and a position of an apex of each of the slanting projections is deviated toward one side in the longitudinal direction from a central position located between both ends of the slanting projection in the longitudinal direction;
   in the projecting-and-depressed region, a first sheet and a second sheet which are layered on one another are joined together at a plurality of joined portions, and the first sheet forms the slanting projections that project in a direction separating from the second sheet at sections other than the joined portions;
   the topsheet includes, as densified portions in the projecting-and-depressed region,
      first joined portions formed by fusion-bonding the first sheet and the second sheet by embossing, and
      second joined portions formed by fusion-bonding the first sheet and the second sheet by embossing; and
   a periphery of each of the slanting projections is surrounded by the first joined portions and the second joined portions each having a shorter length, in the longitudinal direction, than the first joined portion;
   wherein the slanting projections have a laterally-oblong planar-view shape in which a length, in the width direction, of the slanting projections is longer than a length thereof in the longitudinal direction.

2. The absorbent article according to claim 1, wherein the slanting projections are slanted in a state in which a rising section of the slanting projections on the one side, toward which the position of the apex is deviated, is tilted more toward the one side than perpendicular.

3. The absorbent article according to claim 1, wherein the slanting projections include an overhanging section on the one side toward which the position of the apex is deviated.

4. The absorbent article according to claim 1, wherein the position of the apex of one of the plurality of the slanting projections does not go beyond a position of another slanting projection's end that is located on an opposite side from the one side, the another slanting projection being adjacent to the slanting projection on the one side toward which the position of the apex is deviated.

5. The absorbent article according to claim 1, wherein:
   the projecting-and-depressed region includes non-slanting projections in addition to the slanting projections; and
   the non-slanting projections project toward the wearer's skin side, and the position of the apex of each of the non-slanting projections is present at the central position located between both ends, in the longitudinal direction, of the non-slanting projection.

6. The absorbent article according to claim 1, wherein the slanting projections comprises only either forward slanting projections or rearward slanting projections over the entire topsheet or over an entire central region located in a central area, in the width direction, of the topsheet,
   a position of the apex of each of the forward slanting projections is deviated toward the front side from the central position between the both ends, and
   a position of the apex of each of the rearward slanting projections is deviated toward the rear side from the central position.

7. The absorbent article according to claim 1, wherein a surface on the second sheet side is substantially flat, and projections and depressions having large undulations are formed on the first sheet side by the slanting projections and depressions located between the slanting projections.

8. The absorbent article according to claim 1, wherein:
   the projecting-and-depressed region includes a projection row in which a plurality of the slanting projections whose position of the apex is deviated toward the same side in the longitudinal direction are lined up along the longitudinal direction; and
   a depression including a densified portion is provided between the slanting projections in the projection row.

9. The absorbent article according to claim 8, wherein:
   in the projecting-and-depressed region,
   a plurality of width-direction projection rows, in each of which a plurality of the slanting projections are arranged in a line along the width direction at given intervals, are formed in the longitudinal direction, and
   a plurality of projection rows, in each of which a plurality of the slanting projections are arranged in a line along the longitudinal direction at given intervals, are formed in the width direction;
   the first joined portion between the slanting projections that are adjacent to one another in the longitudinal direction in each of the projection rows is located between the slanting projections adjacent to one another in the width direction in each of the width-direction projection rows; and
   the first joined portion between the slanting projections adjacent to one another in the width direction is located between the slanting projections in the projection rows adjacent to one another in the width direction.

10. The absorbent article according to claim 9, wherein the densified portion's density on the opposite side from the one side, toward which the position of the apex is deviated, is higher than the density thereof on the one side.

11. The absorbent article according to claim 9, wherein the projecting-and-depressed region includes, as the width-direction projection rows, a high-rate slanting projection row in which the slanting projections account for half or more of the projections constituting the width-direction projection rows.

12. The absorbent article according to claim 11, wherein, in the width-direction projection rows, the slanting projections account for more than half of the projections.

13. The absorbent article according to claim 11, wherein the projecting-and-depressed region includes a plurality of the high-rate slanting projection rows.

14. The absorbent article according to claim 11, wherein:
   in addition to the high-rate slanting projection row, the projecting-and-depressed region includes, as the width-direction projection rows, a non-high-rate slanting projection row which is either a low-rate slanting projection row in which the rate of the slanting projections is low, or a non-slanting projection row including only non-slanting projections; and the high-rate slanting projection row and the non-high-rate slanting projection row are arranged alternately in the longitudinal direction.

15. The absorbent article according to claim 1, wherein, when the absorbent article's entire length in the longitudinal direction is divided into three equal parts and the absorbent article is divided into a rear portion to be arranged on the wearer's rear side, a front portion to be arranged on the wearer's front side, and a crotch portion located between the front portion and the rear portion, forward slanting projections, whose position of the apex is deviated toward the front side from the central position between the both ends, are formed as the slanting projections in the rear portion.

16. The absorbent article according to claim 1, wherein, in the projecting-and-depressed region, the slanting projections are formed in a dispersed state in the longitudinal direction and the width direction and are arranged in a staggered manner.

17. The absorbent article according to claim 1, wherein:
the projecting-and-depressed region includes an identically-slanting region including a plurality of the slanting projections whose position of the apex is deviated toward the same side in the longitudinal direction; and
in the identically-slanting region, a mean deviation MMD1 of frictional coefficient, in the slanting direction, of the plurality of slanting projections is different from a mean deviation MMD2 of frictional coefficient thereof in an opposite direction from the slanting direction.

18. The absorbent article according to claim 1, wherein:
the projecting-and-depressed region includes an identically-slanting region including a plurality of the slanting projections whose position of the apex is deviated toward the same side in the longitudinal direction; and
in the identically-slanting region, the mean deviation MMD1 of frictional coefficient, in the slanting direction, of the plurality of slanting projections is smaller than the mean deviation MMD2 of frictional coefficient thereof in the opposite direction from the slanting direction.

* * * * *